(12) United States Patent
Stieber et al.

(10) Patent No.: US 6,180,795 B1
(45) Date of Patent: Jan. 30, 2001

(54) PROCESS FOR MAKING N-ALKYL BIS(THIAZOLYL)SULFENIMIDES

(75) Inventors: Joseph F. Stieber, Prospect; Franklin H. Barrows, Waterbury, both of CT (US)

(73) Assignee: Uniroyal Chemical Company, Inc., Middlebury, CT (US)

( * ) Notice: Under 35 U.S.C. 154(b), the term of this patent shall be extended for 0 days.

(21) Appl. No.: 09/365,295

(22) Filed: Jul. 30, 1999

(51) Int. Cl.[7] .................... C07D 417/12; C07D 277/32
(52) U.S. Cl. ..................... 548/158; 548/182; 548/157
(58) Field of Search ................ 548/158, 157, 548/182

(56) References Cited

U.S. PATENT DOCUMENTS

| | | | |
|---|---|---|---|
| 2,860,142 | 11/1958 | Conly | 260/306.6 |
| 3,151,122 | 9/1964 | Sundholm | 260/306.6 |
| 5,079,305 | 1/1992 | Rostek, Jr. | 525/332.7 |
| 5,189,174 | 2/1993 | Rostek, Jr. | 546/255 |
| 5,204,481 | 4/1993 | Carroll et al. | 548/157 |

FOREIGN PATENT DOCUMENTS 574 369 * 12/1993 (EP) ..................... 548/167

OTHER PUBLICATIONS

Ignatov et al., Zhurnal Obshchei Khimii, 47(5):1096–1103 (1977).

* cited by examiner

*Primary Examiner*—Charanjit S. Aulakh
(74) *Attorney, Agent, or Firm*—Raymond D. Thompson; Paul Grandinetti

(57) ABSTRACT

There is disclosed a process for the preparation of sulfenimides comprising: mixing, in a hydrocarbon solvent, a sulfenamide of the formula

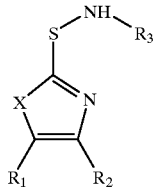

with an aldehyde of the formula $$R_4CHO$$

where X is a sulfur atom, a —C=N— group, or a —C=C— group, $R_1$ and $R_2$ are independently selected from the group consisting of hydrogen, alkyl, and aryl or may be joined to form a saturated or unsaturated ring or aromatic ring, $R_3$ is alkyl or cycloalkyl, and $R_4$ is a hydrocarbon radical wherein the carbon bearing the aldehyde function is bonded only to other carbon atoms, a substituted or unsubstituted aryl ring, or a heteroaromatic ring; and heating the mixture at a temperature and for a period of time sufficient to convert the sulfenamide to the sulfenimide.

8 Claims, No Drawings

PROCESS FOR MAKING N-ALKYL BIS(THIAZOLYL)SULFENIMIDES

BACKGROUND OF THE INVENTION

1. Field of the Invention

The present invention relates to a process for the preparation of N-alkyl sulfenimides. More particularly, the present invention relates to a novel process for converting N-alkyl sulfenamides to N-alkyl sulfenimides.

2. Description of Related Art

Sulfenimides have been used commercially as vulcanization accelerators and are said to be useful as pesticides. Sulfenimides have been made in the past by placing an N-alkyl sulfenamide in an organic solvent and converting the sulfenamide to the sulfenimide by the addition of anhydrous HCl gas. In this case, the amine hydrochloride salt is formed as a by-product. The amine hydrochloride salt is then removed by filtration or extraction and the product is isolated by crystallization and filtration. Alternatively, sulfenimides can be made from N-alkyl sulfenamides by placing the N-alkyl sulfenamide in an anhydrous organic solvent and adding an organic acid anhydride. This reaction produces the desired sulfenimide along with the free acid and the N-alkyl amide corresponding to the N-alkyl group of the starting sulfenamide and the acid anhydride used. Sulfenimides have also been made by the reaction of a sulfenyl chloride with an amine in an anhydrous solvent.

Reactions of sulfenamides with carbonyl compounds have been reported in the past. However, none of the these reactions has been found to produce a sulfenimide as the major product of the reaction.

U.S. Pat. No. 2,860,142 discloses a process for the conversion of sulfenamides to sulfenimides comprising treating an N-alkyl or N-cycloalkyl benzothiazolyl-2-sulfenamide with acetic anhydride or a homolog thereof, with or without the presence of a second solvent, at about 25 to about 75° C., for an appropriate period that can range from about 10 minutes to 24 hours. The resulting sulfenimide is isolated by crystallization, dilution, or by stripping off the solvent. The yields are very good.

U.S. Pat. No. 3,151,122 discloses a process for the preparation of N-alkyl-and N-cycloalkylbis(2-benzothiazolyl)sulfenimides comprising treating the corresponding 2-benzothiazolylsulfenamide under substantially anhydrous conditions with an acid having an ionization constant $K_a$ above $1 \times 10^{-3}$ at 25° C. The compounds are useful as accelerators in the vulcanization of any of the recognized sulfur-vulcanizable rubbers and show good resistance to scorch.

U.S. Pat. Nos. 5,079,305 and 5,189,174 disclose heterocyclic thiol sulfenimide compounds that are said to be useful as accelerators in the curing of natural and/or synthetic rubbers. The compounds can be represented by the formula:

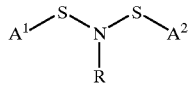

Herein each of $A^1$ and $A^2$, independently, is at least one heterocyclic ring containing one or more nitrogen atoms therein, or at least one heterocyclic ring containing one or more nitrogen atoms and (1) one or more hydrocarbyl substituents; or (2) one or more electron withdrawing groups; or (3) one or more electron releasing groups, wherein $A^1$ alternatively is thiazyl or a dithiocarbamoyl, and wherein R is: (a) a hydrogen atom, or (b) a hydrocarbyl radical having from 1 to 16 carbon atoms, or (c) the hydrocarbon radical of (b) wherein one or more of the carbon atoms is an oxygen atom, a nitrogen atom, or a substituted nitrogen atom wherein the substituted group is an alkyl and, in combination with the nitrogen atom, forms a heterocyclic ring having a total of one to seven carbon atoms, or (d) the hydrocarbyl radical of (b) containing a halogen, an amino, a cyano, an alkoxy, a hydroxy, or an alkoxycarbonyl. When the heterocyclic thiol sulfenimide compound is utilized as an accelerator for rubber, improved cure rates, longer scorch delay, and better reversion resistance are said to be obtained in comparison to conventional sulfenamides.

U.S. Pat. No. 5,204,481 discloses a process for producing N-alkyl or N-cycloalkyl-2-benzothiazolyl sulfenimides wherein aliphatic hydrocarbons are used as a reaction medium in converting N-alkyl or N-cycloalkyl-2-benzothiazolyl sulfenamides to the corresponding sulfenimides by reaction with an acid.

Ignatov et al., *Zhurnal Obshchei Khimii*, 47(5): 1096–1103 (1977) studied the reactions of 2-benzothiazolylsulfeneamide and N-cyclohexyl-2-benzothiazolylsulfenamide with acetic acid, acetyl chloride, acetic anhydride, benzoyl chloride, picryl chloride, butyl acetate, maleic anhydride, phthalic anhydride, hydrochloric acid, trichloroacetic acid, thioacetic acid, and hydrogen sulfide. This enabled the authors to determine the optimum conditions for the synthesis of bis-2-benzothiazolylsulfenimide and N-cyclohexyl bis(2-benzothiazolyl)sulfenimide, which compounds are said to have valuable properties as general purpose rubber vulcanization accelerators.

The disclosures of the foregoing are incorporated herein by reference in their entirety.

SUMMARY OF THE INVENTION

In the process of the present invention, a sulfenamide is converted to a sulfenimide by a reaction with an aldehyde. The process is carried out by placing an N-alkyl sulfenamide in an appropriate organic solvent, then adding a stoichiometric excess of an aldehyde, heating the mixture to boiling and removing the water formed in the reaction until the reaction is complete. The product thus formed can be isolated by filtration from the reaction mixture or by evaporation of the reaction solvent, followed by crystallization of the crude reaction product, and filtration from a suitable solvent.

More particularly, the present invention is directed to a process for the preparation of sulfenimides comprising:
mixing, in a hydrocarbon solvent, a sulfenamide of the formula

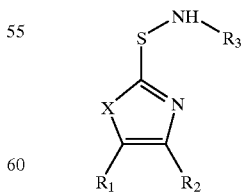

with an aldehyde of the formula $R_4 CHO$ where X is a sulfur atom, a —C=N— group, or a —C=C— group, $R_1$ and $R_2$ are independently selected from the group consisting of hydrogen, alkyl, and aryl or may be joined to form a saturated or unsaturated ring or aromatic ring, $R_3$ is alkyl or cycloalkyl, and $R_4$ is a hydrocarbon radical wherein the carbon bearing the aldehyde function is bonded only to other carbon atoms, a substituted or unsubstituted aryl ring, or a heteroaromatic ring; and heating the mixture at a temperature and for a period of time sufficient to convert the sulfenamide to the sulfenimide.

The reaction can be represented by the equation:

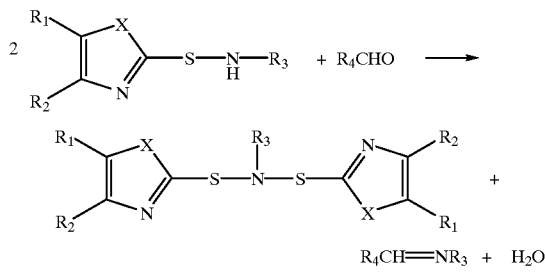

In a particularly preferred embodiment, the reaction can be represented by the equation:

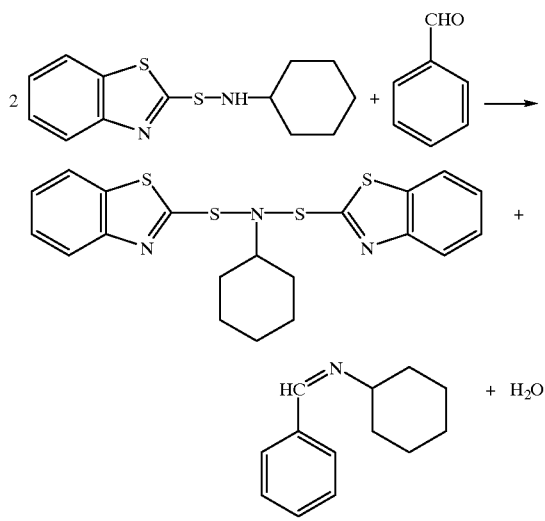

In light of the reported reaction of N-cyclohexyl 2-benzothiazolylsulfenamide with acetone, and the reaction of 2-benzothiazolylsulfenamide with cyclohexanone, the reaction of N-cyclohexyl 2-benzothiazolylsulfenamide with an aldehyde to form N-cyclohexyl bis(2-benzothiazolyl) sulfenimide in high yield is surprising and unexpected.

DESCRIPTION OF THE PREFERRED EMBODIMENTS

As disclosed above, the present invention is directed to a process for preparing a sulfenimide by reacting a sulfenamide of the structure:

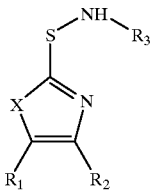

with an aldehyde of the structure $R_4CHO$.

In the formula for the sulfenamide, X is a sulfur atom, a —C=N— group, or a —C=C— group. Thus, the ring shown in the formula will be of one of the following structures:

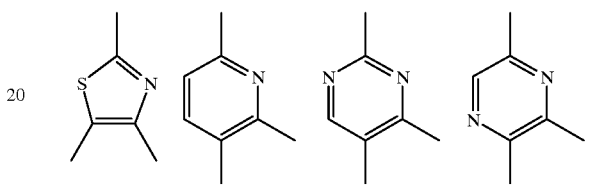

$R_1$ and $R_2$ in the formula can be the same or different and can be hydrogen, alkyl, or aryl, or can be joined to form a saturated or unsaturated ring or an aromatic ring. Where they can be straight or branched chain alkyl, which term is intended to include cycloalkyl, they are preferably of 1 to 12 carbon atoms, e.g., methyl, ethyl, propyl, butyl, pentyl, hexyl, heptyl, octyl, nonyl, decyl, undecyl, dodecyl, cyclopentyl, cyclohexyl, cycloheptyl, isomers of the foregoing, and the like. It is preferred that, where $R_1$ and/or $R_2$ are alkyl, they are alkyl of one to eight carbon atoms, and more preferred that they are of one to four carbon atoms. Those skilled in the art will realize that where $R_1$ and/or $R_2$ are cycloalkyl, the cycloalkyl ring may be substituted, typically with one or more alkyl groups, generally lower alkyl groups, such as methyl, ethyl, propyl, butyl, isomers thereof, and the like.

Where $R_1$ and/or $R_2$ are aryl, they are preferably aryl of 6 to 12 carbon atoms, e.g., phenyl, naphthyl, anthryl, phenanthryl, and the like, which may be substituted or unsubstituted. Phenyl is preferred.

Where $R_1$ and/or $R_2$ are joined to form a saturated or unsaturated ring or an aromatic ring, the ring so formed is preferably one having five, six, or seven members, which members may be carbon, nitrogen, oxygen, or sulfur. The ring may be substituted with any substituent that will not adversely affect the properties of the sulfenimide to be formed for the application to which it is to be put. It is most preferred that such a ring, when present, be phenyl.

In the formula for the sulfenamide, $R_3$ is a straight or branched chain alkyl moiety, which term is intended to include cycloalkyl, preferably of 1 to 12 carbon atoms, e.g., methyl, ethyl, propyl, butyl, pentyl, hexyl, lieptyl, octyl, nonyl, decyl, undecyl, dodecyl, cyclopentyl, cyclohexyl, cycloheptyl, isomers of the foregoing, and the like. It is preferred that $R_3$ be alkyl of one to eight carbon atoms, and more preferred that it be of one to four carbon atoms. Those skilled in the art will realize that where $R_3$ is cycloalkyl, the cycloalkyl ring may be substituted, typically with one or more alkyl groups, generally lower alkyl groups, such as methyl, ethyl, propyl, butyl, isomers thereof and the like.

Preferably, the N-alkyl sulfenamide used as the starting material has the formula:

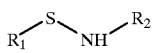

wherein $R_1$ is 2-benzothiazolyl, 2-pyridyl, 2-pyrimidyl, or 4,5-substituted 2-thiazolyl and $R_2$ is a substituted or unsubstituted alkyl group, which term is intended to include cycloalkyl. More preferably, the N-alkyl sulfenamide starting material is selected from the group consisting of:
N-cyclohexyl-2-benzothiazolylsulfenamide,
N-tert-butyl-2-benzothiazolylsulfenamide,
N-isopropyl- 2-benzothiazolylsulfenamide,
N-tert-octyl-2-benzothiazolylsulfenamide,
N-sec-butyl-2-benzothiazolylsulfenamide,
N-iso-butyl-2-benzothiazolylsulfenamide,
N-tert-amyl-2-benzothiazolylsulfenamide,
N-iso-amyl-2-benzothiazolylsulfenamide,
N-(2-ethylhexyl)-2-benzothiazolyl sulfenamide,
N-cyclohexyl-2-pyridylsulfenamide,
N-tert-butyl-2-pyridylsulfenamide,
N-isopropyl-2-pyridylsulfenamide,
N-tert-octyl-2-pyridylsulfenamide,
N-sec-butyl-2-pyridylsulfenamide,
N-iso-butyl-2-pyridylsulfenamide,
N-tert-amyl-2-pyridylsulfenamide,
N-iso-amyl-2-pyridylsulfenamide,
N-(2-ethylhexyl) -2-pyridylsulfenamide,
N-cyclohexyl-2-pyrimidylsulfenamide,
N-tert-butyl-2-pyrimidylsulfenamide,
N-isopropyl-2-pyrimidylsulfenamide,
N-tert-octyl-2-pyrimidylsulfenamide,
N-sec-butyl-2-pyrimidylsulfenamide,
N-iso-butyl-2-pyrimidylsulfenamide,
N-tert-amyl-2-pyrimidylsulfenamide,
N-iso-amyl-2-pyrimidylsulfenamide,
N-(2-ethylhexyl)-2-pyrimidylsulfenamide,
N-cyclohexyl-2-(4-phenyl)thiazolylsulfenamide,
N-tert-butyl-2-(4-phenyl)thiazolylsulfenamide,
N-isopropyl-2-(4-phenyl)thiazolylsulfenamide,
N-tert-octyl-2-(4-phenyl)thiazolylsulfenamide,
N-sec-butyl-2-(4-phenyl)thiazolylsulfenamide,
N-iso-butyl-2-(4-phenyl)thiazolylsulfenamide,
N-tert-amyl-2-(4-phenyl)thiazolylsulfenamide,
N-iso-amyl-2-(4-phenyl)thiazolylsulfenamide, and
N-(2-ethylhexyl)-2-(4-phenyl)thiazolylsulfenamide.

In the practice of the present invention, aldehydes are used to convert the sulfenamides to sulfenimides. These aldehydes are of the structure $R_4$—CHO, in which $R_4$ is a hydrocarbon radical wherein the carbon bearing the aldehyde function is bonded only to other carbon atoms, a substituted or unsubstituted aryl ring, or a heteroaromatic ring. More specifically, $R_4$ may be an aromatic ring which may be substituted with alkyl, hydroxyl, alkoxy, or ester groups. It may also be a heterocyclic ring, provided that the ring carbon atom bearing the aldehyde function has no other substituents. $R_4$ may also be an alkyl group, provided that the carbon atom linked to the aldehyde function is completely substituted with other alkyl groups. Examples of aldehydes useful in this invention are benzaldehyde, salicylaldehyde, 4-isopropylbenzaldehyde, 2-methoxybenzaldehyde, 4-methoxybenzaldehyde, 2-furaldehyde, and trimethylacetaldehyde.

A representative sampling of some of the products that may be made by means of the process of the present invention is listed below:
N-cyclohexyl bis(2-benzothiazolyl)sulfenimide,
N-tert-butyl bis(2-benzothiazolyl)sulfenimide,
N-isopropyl bis(2-benzothiazolyl)sulfenimide,
N-tert-octyl bis(2-benzothiazolyl)sulfenimide,
N-sec-butyl bis(2-benzothiazolyl)sulfenimide,
N-iso-butyl bis(2-benzothiazolyl)sulfenimide,
N-tert-amyl bis(2-benzothiazolyl)sulfenimide,
N-iso-amyl bis(2-benzothiazolyl)sulfenimide,
N-(2-ethylhexyl) bis(2-benzothiazolyl)sulfenimide,
N-cyclohexyl bis(2-pyridyl)sulfenimide,
N-tert-butyl bis(2-pyridyl)sulfenimide,
N-isopropyl bis(2-pyridyl)sulfenimide,
N-tert-octyl bis(2-pyridyl)sulfenimide,
N-sec-butyl bis(2-pyridyl)sulfenimide,
N-iso-butyl bis(2-pyridyl)sulfenimide,
N-tert-amyl bis(2-pyridyl)sulfenimide,
N-iso-amyl bis(2-pyridyl)sulfenimide,
N-(2-ethylhexyl) bis(2-pyridyl)sulfenimide,
N-cyclohexyl bis(2-pyrimidyl)sulfenimide,
N-tert-butyl bis(2-pyrimidyl)sulfenimide,
N-isopropyl bis(2-pyrimidyl)sulfenimide,
N-tert-octyl bis(2-pyrimidyl) sulfenimide,
N-sec-butyl bis(2-pyrimidyl)sulfenimide,
N-iso-butyl bis(2-pyrimidyl) sulfenimide,
N-tert-amyl bis(2-pyrimidyl) sulfenimide,
N-iso-amyl bis(2-pyrimidyl) sulfenimide,
N-(2-ethylhexyl) bis(2-pyrimidyl)sulfenimide,
N-cyclohexyl bis[2-(4-phenyl)thiazolyl]sulfenimide,
N-tert-butyl bis[2-(4-phenyl)thiazolyl]sulfenimide,
N-isopropyl bis[2-(4-phenyl)thiazolyl]sulfenimide,
N-tert-octyl bis[2-(4-phenyl)thiazolyl]sulfenimide,
N-sec-butyl bis[2-(4-phenyl)thiazolyl]sulfenimide,
N-iso-butyl bis[2-(4-phenyl)thiazolyl]sulfenimide,
N-tert-amyl bis[2-(4-phenyl)thiazolyl]sulfenimide,
N-iso-amyl bis[2-(4-phenyl)thiazolyl]sulfenimide, and
N-(2-ethylhexyl) bis[2-(4-phenyl)thiazolyl]sulfenimide.

The process of the present invention is carried out by placing an N-alkyl sulfenamide in an appropriate organic solvent, then adding a stoichiometric excess of an aldehyde, heating the mixture to boiling, and removing the water formed in the reaction until the reaction is complete. The product thus formed can be isolated by filtration from the reaction mixture or by evaporation of the reaction solvent, followed by crystallization of the crude reaction product and filtration from a suitable solvent.

The reaction solvents useful in the process of the present invention can be aliphatic hydrocarbons, which may be straight chain, branched chain, or cyclic; aromatic hydrocarbons, in which the aromatic ring may be substituted with alkyl groups or halogens; dialkyl ethers; or halogenated aliphatic hydrocarbons. Examples of solvents that can be used include hexane, heptane, octane, isooctane, cyclohexane, toluene, xylene, chlorobenzene, chloroform, methylene chloride, ethylene dichloride, methyl chloroform, tetrahydrofuran, diethyl ether, and the like.

Processes currently known in the art typically use either anhydrous hydrogen chloride, or an acid anhydride to convert sulfenamides to sulfenimides. A by-product in the case of the anhydrous HCl is the amine hydrochloride corresponding to the sulfenamide used. In the case of the acid anhydrides, a by-product is the amide corresponding to the acid anhydride and the amine portion of the starting sulfenamide employed. Handling anhydrous HCl gas (and other strong mineral acids or acidic materials that can induce the desired transformation) is, however, a hazardous operation requiring special equipment to vaporize and transport the gas and to protect workers from the extremely corrosive and toxic material. Further, the amine hydrochloride by-product must be separated from the reaction mixture and then recovered by neutralization with a base, generating a salty waste stream.

Where acid anhydrides are employed, the reagent is of a lower order of acute toxicity but is still corrosive to bodily tissues and must be handled with care. Again, the by-product amides must be hydrolyzed with acid or base to regenerate the amine, leaving the acid as a waste stream that must be discarded or subjected to further processing to regenerate the anhydride.

It is an advantage of the present invention that the aldehydes used as one of the reactants are not corrosive, as are the acids and acid anhydrides used in the prior art. Thus, they are easier to handle in a manufacturing environment and are noncorrosive to most commonly used metal equipment. A by-product of the reaction of the present invention is the imine corresponding to the amine of the sulfenamide and the aldehyde starting materials employed. This by-product is easy to wash off the product and can easily be reconverted back to the starting aldehyde and the amine by simply boiling the by-product with water and a small amount of acid as a catalyst. The raw materials may then be isolated by a simple distillation. The amine thus generated can be used to produce more of the starting sulfenamide and the aldehyde can be recycled to produce more sulfenimide. Accordingly, the process of the present invention advantageously produces very little in the way of waste that must be discarded.

In greater detail, to prepare sulfenimides according to the process of the present invention, the sulfenamide used as the starting material is placed in a reaction vessel equipped with an overhead condenser along with a solvent that is inert with respect to all the reactants. The vessel must be able to be heated to the boiling point of the solvent employed, and arranged so that the water produced in the reaction may be separated from the liquid as it refluxes. The concentration of the starting sulfenamide is chosen so that the reaction mixture can be stirred and so that the slurry of the final product in the reaction mixture will be fluid enough to permit easy processing. In practice, the concentration of starting sulfenamide in the solvent will be generally less than 50 weight percent. The aldehyde is added to the mixture of sulfenamide and solvent. The mole ratio of aldehyde to the starting sulfenamide must be at least 0.5:1.0, and preferably should be at least 0.75:1.0 or more. However, a molar ratio greater than 1.5:1.0 has no beneficial effect and may hinder the isolation of the final product. The reaction mixture is then heated and stirred until it boils and distillate collects in the overhead condenser. Water is separated from the refluxing liquid, and the dry condensate may be returned to the reaction. This refluxing process is continued until no more water separates from the refluxing liquid, or until chromatographic analysis of the reaction mixture shows that the reaction is complete. The reaction mixture is then cooled to near ambient temperature, whereupon the sulfenimide product crystallizes and can then be isolated by filtration and dried.

The rate and extent of the reaction can be improved by the addition of a small amount of an acid catalyst at the start of the reaction. The acid catalyst can be a strong Lewis acid, such as anhydrous aluminum trichloride, or a weak organic acid, such as benzoic acid. Strong acids are known to react with sulfenamides to form sulfenimides when used in stoichiometric equivalent amounts, but in the practice of the present invention, much smaller amounts, about one weight percent of the reagents, are effective in accelerating the rate of the reaction.

Other materials can also accelerate the rate of the transformation. Surprisingly, the addition of a quantity of anhydrous calcium chloride will accelerate the reaction nearly as well as the addition of an acid. As little as one percent by weight of calcium chloride has a noticeable effect. The degree of enhancement increases as the loading of calcium chloride increases. The rate enhancement is not due simply to the desiccant property of the anhydrous salt, since the water evolved in the reaction still collects with the distillate; and in a comparative reaction, the addition of a different drying agent, anhydrous sodium sulfate, had no effect on the reaction.

When an inorganic solid, such as calcium chloride, is used, the reaction mixture may be filtered while it is still hot and the product is in solution, in order to remove the salt so that it will not contaminate the organic product.

The advantages and important features of the present invention will be more apparent from the following examples.

EXAMPLE 1

Preparation of N-cyclohexyl bis(2-benzothiazolyl) sulfenimide using benzaldehyde A glass reaction flask was assembled with a mechanical paddle stirrer, a Dean-Stark trap with a water-cooled condenser arranged for reflux, a thermocouple, and an electric heating mantle. The flask was charged with 52.6 grams of N-cyclohexyl 2-benzothiazolylsulfenamide, 150 mL of heptane, and 21.2 grams of benzaldehyde. The mixture was stirred and heated to the boiling point. As the mixture boiled and the reaction progressed, water collected in the bottom of the Dean-Stark trap. The extent of the reaction was determined by measuring the amount of water collected in the trap and by periodically removing small samples of the reaction solution for analysis by high performance liquid chromatography. The process continued until approximately 95 percent of the starting sulfenamide was converted to the desired sulfenimide. This required 11 hours. The reaction mixture was cooled to ambient temperature, and the product formed a crystalline precipitate. The solid product was filtered and washed with a quantity of fresh heptane and thoroughly dried. The yield of product was 38.5 grams, 89.7 percent of the theoretical yield.

EXAMPLE 2

Preparation of N-cyclohexyl bis(2-benzothiazolyl) sulfenimide using benzaldehyde and benzoic acid catalyst An apparatus was assembled as in Example 1. The flask was charged with 52.6 grams of N-cyclohexyl 2-benzothiazolylsulfenamide, 150 nL of heptane, 21.2 grams of benzaldehyde, and 1.1 grams of benzoic acid. The mixture was heated as in Example 1. In this case, the reaction required only five hours of heating to achieve 95 percent conversion to products. The yield of filtered, washed, and dried product was 38.5 grams, 89.7 percent yield.

EXAMPLE 3

Preparation of N-cyclohexyl bis(2-benzothiazolyl) sulfenimide using 2-furaldehyde An apparatus was assembled as in Example 1. The flask was charged with 52.6 grams of N-cyclohexyl 2-benzothiazolylsulfenamide, 150 mL of heptane, and 19.2 grams of 2-furaldehyde. The mixture was heated as in Example 1. In this case the reaction required 10 to 12 hours of heating to achieve 95 percent conversion to products. The yield of filtered, washed, and dried product was 38.1 grams, 88.8 percent yield.

EXAMPLE 4

Preparation of N-tert-butyl bis(2-benzothiazolyl) sulfenimide using benzaldehyde An apparatus was assembled as in Example 1. The flask was charged with 47.2 grams of N-tert-butyl-2-benzothiazolylsulfenamide, 150 niL of heptane, and 21.2 grams of benzaldehyde. The reaction mixture was heated as in Example 1. In this case the reaction required nearly 20 hours to proceed to 70 to 80 percent conversion. The product was isolated and dried as in Example 1. The yield of product was 27.7 grams, 68.7 percent of the theoretical yield.

EXAMPLE 5

Preparation of N-cyclohexyl bis[2-(4-phenyl) thiazolyl]sulfenimide using benzaldehyde An apparatus was set up as in Example 1. The flask was charged with 29.0 grams of N-cyclohexyl-2-(4-phenyl) thiazolylsulfenamide, 75 niL of heptane, 30 10.6 grams of benzaldehyde, and 0.55 gram of benzoic acid. The reaction mixture was heated as in Example 1. The reaction required nine hours to reach approximately 95 percent conversion. The product was isolated and dried as in Example 1. The yield was 18.1 grams, 75.3 percent of theory.

In view of the many changes and modifications that can be made without departing from principles underlying the invention, reference should be made to the appended claims for an understanding of the scope of the protection to be afforded the invention.

What is claimed is:

1. A process for the preparation of sulfenimides comprising: mixing, in an organic solvent, a sulfenamide of the formula

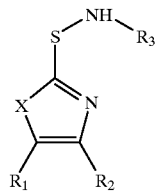

with an aldehyde of the formula $$R_4CHO$$

where X is a sulfur atom, $R_1$ and $R_2$ are independently selected from the group consisting of hydrogen, alkyl, and aryl or may be joined to form a saturated or unsaturated ring or aromatic ring, $R_3$ is alkyl or cycloalkyl, and $R_4$ is a hydrocarbon radical wherein the carbon bearing the aldehyde function is bonded only to other carbon atoms, a substituted or unsubstituted aryl ring, or a heteroaromatic ring; and heating the mixture at a temperature and for a period of time sufficient to convert the sulfenamide to the sulfenimide.

2. A process as described in claim 1, in which the sulfenamide is N-alkyl-2-benzothiazolylsulfenamide or N-alkyl-2-(4-phenyl)thiazolylsulfenamide, and the alkyl group is cyclohexyl, tert-butyl, isopropyl, tert-octyl, sec-butyl, iso-butyl, tert-amyl, iso-amyl, or 2-ethylhexyl.

3. A process as described in claim 1, in which the aldehyde is benzaldehyde, 2-furaldehyde, salicylaldehyde, 4-isopropylbenzaldehyde, 2-methoxybenzaldehyde, 4-methoxybenzaldehyde, or trimethylacetaldehyde.

4. A process as described in claim 1, in which the solvent is hexane, heptane, octane, isooctane, cyclohexane, toluene, xylene, chlorobenzene, choroform, methylene chloride, ethylene dichloride, methyl chloroform, tetrahydrofuran, or diethyl ether.

5. A process as described in claim 1, with the addition of less than 0.1 mole of an acid catalyst per mole of the sulfenamide used.

6. A process as described in claim 1, with the addition of less than one mole of calcium chloride per mole of the sulfenamide used.

7. A process as described in claim 1 in which the sulfenamide is N-cyclohexyl-2-benzothiazolylsulfenamide, or N-tert-butyl-2-benzothiazolylsulfenamide, N-isopropyl-2-benzothiazolylsulfenamide, N-tert-octyl-2-benzothiazolylsulfenamide, the aldehyde is benzaldehyde, or 2-furaldehyde, and the solvent is hexane, heptane, octane, isooctane, cyclohexane, toluene, or xylene.

8. A process as described in claim 1 in which the solvent, aldehyde, and amine are recovered from the reaction mother liquors by an acid catalyzed hydrolysis followed by fractional distillation of the components.

* * * * *